United States Patent [19]
Groner et al.

[11] Patent Number: 5,858,697
[45] Date of Patent: Jan. 12, 1999

[54] METHOD FOR RAPID DIAGNOSTIC OF URINARY TRACT INFECTIONS

[75] Inventors: Warren Groner, Great Neck, N.Y.; Jean-Louis Drocourt, Yerres; Louis Foissac, Neuilly Sur Seine, both of France

[73] Assignee: Chemunex, Maisons-Alfort, France

[21] Appl. No.: 667,014

[22] Filed: Jun. 20, 1996

[30] Foreign Application Priority Data

Jun. 22, 1995 [EP] European Pat. Off. .............. 95401483

[51] Int. Cl.$^6$ .............................. C12Q 1/04; C12Q 1/02; C12Q 1/00; G01N 33/53
[52] U.S. Cl. .................................. 435/34; 435/29; 435/4; 435/19; 435/968; 435/973; 435/7.24; 435/7.32; 549/223
[58] Field of Search .................................. 435/34, 19, 29, 435/4, 968, 973, 7.24, 7.32; 549/223

[56] References Cited

U.S. PATENT DOCUMENTS

| | | | |
|---|---|---|---|
| 4,581,334 | 4/1986 | Kirchanskie et al. | 435/29 |
| 4,622,298 | 11/1986 | Mansour et al. | 435/34 |
| 4,657,855 | 4/1987 | Corey et al. | 435/19 |
| 5,325,168 | 6/1994 | Nakamoto et al. | 435/34 |
| 5,464,739 | 11/1995 | Johnson et al. | 435/4 |

FOREIGN PATENT DOCUMENTS

| | | |
|---|---|---|
| 333561 | 9/1989 | European Pat. Off. . |
| 405480 | 1/1991 | European Pat. Off. . |
| 443700 | 8/1991 | European Pat. Off. . |
| 515099 | 11/1992 | European Pat. Off. . |

*Primary Examiner*—Louise N. Leary
*Attorney, Agent, or Firm*—Bell Seltzer Intellectual Property Group of Alston & Bird, LLP

[57] ABSTRACT

Method for the rapid diagnostic of an infection of the urinary tract (UTI), by a specific examination of urine.

The method of analyzing a urine specimen, for the rapid and simultaneous counting of both viable bacteria and leucocytes (white blood cells or WBC), consists of:

(1) simultaneous labeling of said bacteria and said white blood cells (WBC) present in said urine specimen, with a fluorescent viability marker of bacteria, said marker tagging and accumulating in both bacteria and white blood cells, under the same conditions and leading to different fluorescent elements;

(2) automatically counting all the fluorescent elements by photoelectric detection of the fluorescent marker; and (3) simultaneously classifying said fluorescent elements in fluorescent viable bacteria and in fluorescent white blood cells, in view to obtain in one part the total number of bacteria and on the other part, the total number of white blood cells, on the basis of their size.

22 Claims, 2 Drawing Sheets

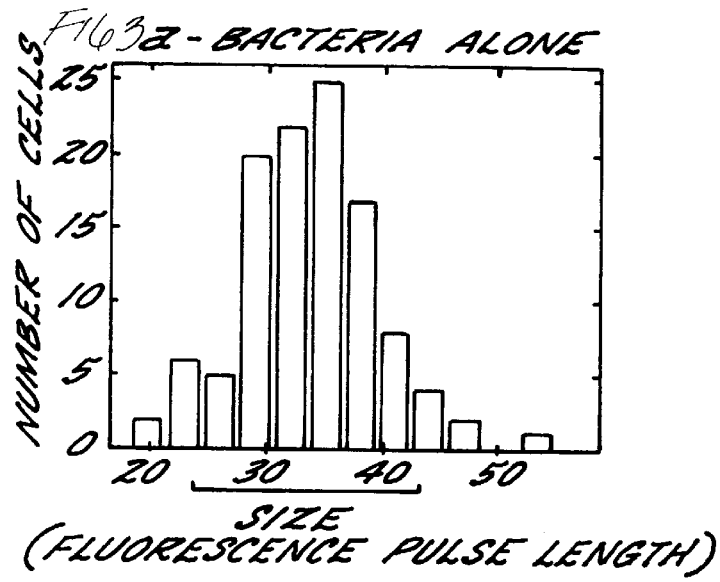
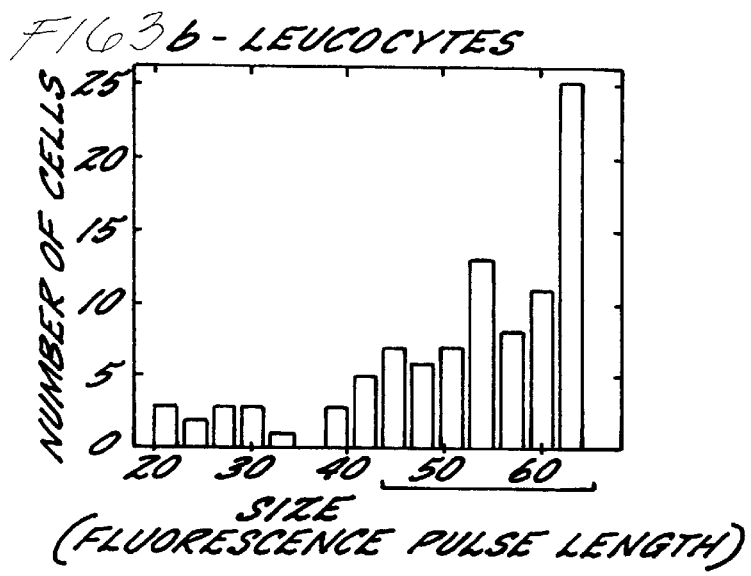
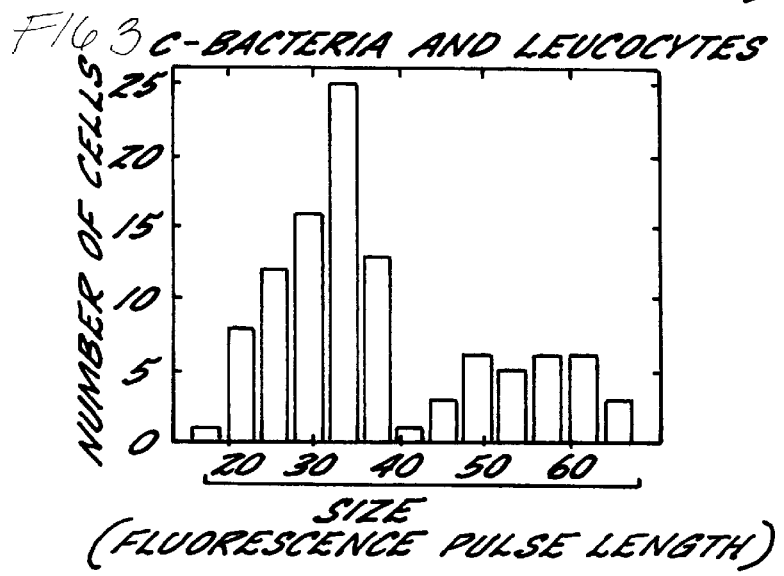

METHOD FOR RAPID DIAGNOSTIC OF URINARY TRACT INFECTIONS

The instant invention relates to a method for the rapid diagnostic of an infection of the urinary tract (UTI), by a specific examination of urine.

Two laboratory findings are more particularly carried out in case of an infection of the urinary tract, i.e. count of white blood cells (pyuria) and culture of microorganisms (bacteriuria).

These two tests present independent diagnosis value:
bacteriuria without pyuria indicates contamination of the specimen or colonization of the bacteria in the urine without tissue invasion.
pyuria without bacteriuria indicates inflammation without infection or may sometimes reveal the presence of anaerobic bacteria.

However, the clinical synergy of these two findings is frequently mitigated by laboratory practice since they are generally the result of two separate tests frequently performed at different times and upon different samples; such a situation leads, therefore to a very difficult comparison and interpretation of the results.

Generally, pyuria is evaluated by the determination of the number of white blood cells in a urine sample, as part of the microscopic examination of the solid material in urine (high power field), concentrated by sedimentation. However, this method has been shown to be imprecise, poorly correlated with the excretion rates of leucocytes, not reproducible and time-consuming. The major source of inaccuracy and imprecision has been found to be a result of the sedimentation process where there is a poor relationship between the volume examined and the amount of original sample (Am. J. Med., 1983, 53–58). Alternatively, the undiluted urine could be analyzed for leucocyte alkaline phophatase, on a serum chemistry analyzer; however, this method is not sufficiently sensitive.

More quantitative results which were obtained by counting leucocytes with a hemocytometer, in unspun urine, have been shown to correlate better with excretion rates and with urinary tract infection (Blum et al. J. Gen. Int. Med., 1992, 140–144) It is however time-consuming and it may not be routinely available.

However, these methods are difficult to perform, more costly and may not be sufficiently sensitive, given the relatively low concentration of white blood cells in normal urine (<10,000 per ml).

Bacteriuria is, generally, detected by cultures, which constitute the standard process for the diagnosis of UTI. However, such a procedure is expensive and the results are not readily available since the test requires one to two days for obtaining a positive result and there is as much as seven days for a confirmed negative result.

Such a delay in diagnosis constitutes a major drawback in so far as a rapid diagnosis allows a prompt treatment and can avoid renal damage especially in small children and infants.

More rapid methods of detection of bacteria in urine have been proposed such as Gram staining and ATP bioluminescence (Pezzlo et al., J. Clin. Microbiol., 1989, 716–720); however, such methods generally do not offer the sensitivity of the culture methods. Indeed, desired detection sensitivity to viable bacteria is less than 10,000 per ml.

Thus, the required sensitivity of detection for medical use is similar for bacteria and white blood cells (WBC) and is generally not achieved with the rapid methods of detection.

In view to overcome the hereabove mentioned difficulties, there have been many methods proposed and used for rapid screening of urine to detect UTI. These methods include, for instance:

rapid dipstick tests reacting to esterase activity of both leucocytes and bacteria; (Blum et al, cited; Bachman et al., JAMA, 1993, 270, 6, 1971–1974; Pezzlo et al. cited); however, they provide no distinction between leucocytes and bacteria, and the sensitivity is limited. For example, bacteriuria at levels of $10^2$ to $10^3$ CFU/ml are detected in less than 50% of the cases, Gram staining Filtration methods (Pezzlo et al. cited) and quantitative microscopy for leucocyte.

A comparison of the results of dipstick analysis, standard microscopic urinalysis, hemocytometric cell counting and Gram staining were compared with the results of a standard urine culture (Blum et al, cited). The standard urinalysis (microscopic analysis of a centrifuged specimen) was the most accurate single method to predict significant bacteriuria in symptomatic ambulatory women. A further comparison with bioluminescence method was illustrated in Pezzlo et al. (cited).

Recent studies have proposed the counting of leucocytes and bacteria, by visual microscopy performed quantitatively on unspun urine specimens (Vickers et al., The Lancet, 1991, 338, 8770, 767–770; Hiraoka et al., Scand. J; Clin. Lab. Invest., 1993, 53, 705–709)). In these studies, the best results are obtained when visual identification is made of both the bacteria and leucocytes, usually with no specific staining.

Even though it is stated (Hiraoka et al., cited) that urine microspopy on a disposable counting chamber is simple, sensitive and time- and cost-saving method for the diagnosis of UTI caused by a variety of bacterial species including cocci, the method suffers from some shortcomings:

sensitivity was less than culture method at low concentrations of bacteria, there is no discrimination between viable and nonviable bacteria leading to false positives which require culture to follow-up, the method is labor intensive and requires trained operators and special optical devices such as a mirrored slide or phase contrast objective lens to be easily and reproducibility performed.

To allow automation of the microscopic analysis of urine, techniques carrying out image analysis on sedimented urine or cell counting have been proposed (Deindoerfer et al., Clin. Chem., 1982, 28, 9, 1910–1916;

Elin et al., Am. J. Clin. Pathol., 1986, 86, 731–737). These systems count and classify the larger particles such as blood cells, casts and crystals, but cell counting systems do not have the ability to discriminate between particles with the view to detect small bacteria. Thus, their predictive value for UTI is quite low. They also suffer from the problems of quantitation on a sedimented sample.

Indeed UTI, where there is less than $10^5$ CFU/ml urine, is very difficult to detect with the hereabove mentioned rapid methods (acute urethral syndrome, for instance) and a concomitant pyuria is quite necessary. It is important, therefore to assess the leucocytes in urine. However none of the hereabove methods allow a simultaneously quantitative detection of bacteria and more specifically viable bacteria and leucocytes.

To sum up the drawbacks of the hereabove technics:
direct detection of bacteria in urine 1. Automated culture method: these methods are sensitive and classify bacteria, but they are slow and give no information about pyuria (WBC) which has been found to be useful clinically and practically (to eliminate false positive results).

2. Microscope analysis on sediment: whether automated or not, the problem is that this test does not give information on viable bacteria. Also the measurement of pyuria is not accurate, because of the sedimentation, and consequently does not correlate with UTI.
3. Cell counters: said counters can detect bacteria, only if present at high concentrations; however, they cannot discriminate viable bacteria.
4. Filters and papers: these methods are rapid and gain sensitivity by sensing both the somatic cells (WBC, RBC, etc . . . ) as well as bacteria. However, since they can not quantify them separately, they loose both the clinical and practical advantages of separate counting of bacteria and WBC.
5. Bioluminescence methods: these methods detect both viable and non viable bacteria. However, somatic cells must be eliminated first as they represent a tremendous interference even at normal levels; moreover even though said technic is rapid, it is quite not sensitive and
6. Dipsticks: even though said technic is rapid, it is quite not sensitive.

indirect detection of bacteria in urine, by evaluation of pyuria 1. microscope analysis on sediment: the measurement of pyuria is not accurate, because of the sedimentation, and consequently does not correlate with UTI.
2. microscope analysis on unspun urine: it is hard to recognize the different elements from each other (WBC or bacteria); moreover, the elements present at low frequency are also very hard to detect (bacteria, for instance).
3. cell counters: said counters can count WBC, however in general category only; therefore, the different categories of white cells cannot be distinguished, whereas it could be important to specifically distinguish for instance polymorphonuclear neutrophils (PMN).
4. Filters and papers (see hereabove).
5. Automated image analysis (AIM): this method allows the count and the classification of WBC; however, it is not accurate.
6. Dipsticks: even though said technic is rapid, it is quite not sensitive (see above).

BRIEF DESCRIPTION OF THE DRAWINGS

FIG. 3(a) is an analysis of a urine sample spiked with bacteria;

FIG. 3(b) is an analysis of a urine sample spiked with human leukocytes, and

FIG. 3(c) is an analysis of a urine sample spiked with both bacteria and leukocytes.

Figure 1:
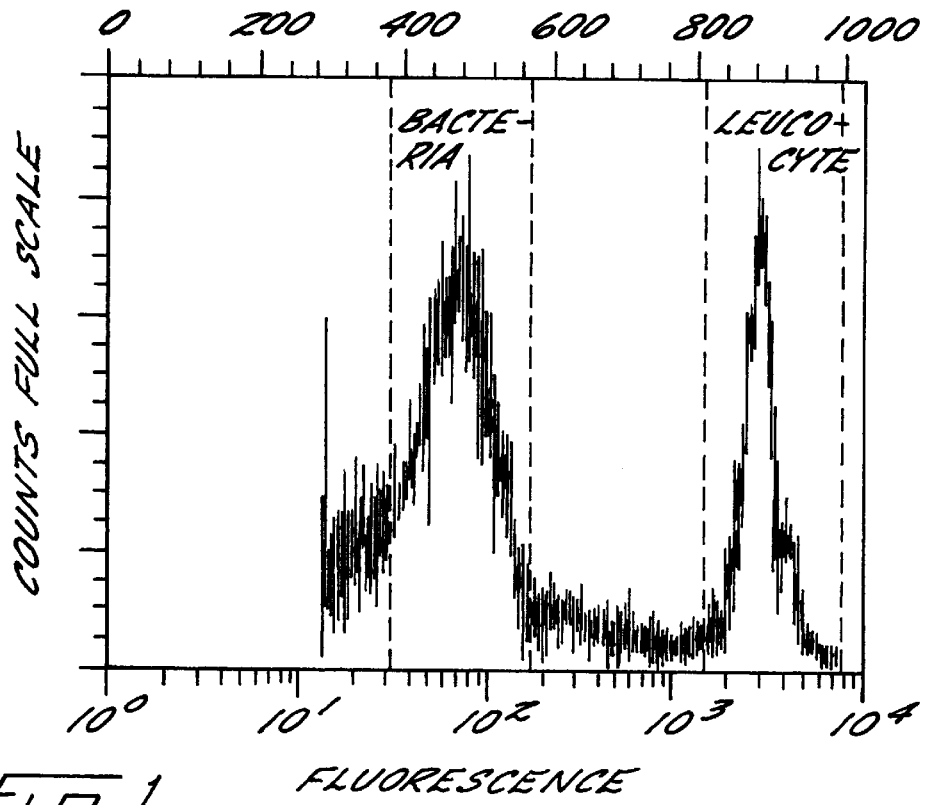
FIG. 1 is a graph showing fluorescence of a urine sample spiked with a bacteria and human blood leukocytes.

Therefore, the aim of the Applicant was consequently to provide a method of detection of bacteria and leucocytes in the same specimens of urine which meets practical needs better than the methods of the prior Art as exposed hereabove, especially by making it possible a simultaneous detection and counting of viable bacteria and white blood cells, without carrying out a bacteria culture and without compulsory sedimentation of the specimen of urine.

The present invention relates to a method of analyzing a urine specimen, characterized in that for the rapid and simultaneous counting of both viable bacteria and leucocytes (white blood cells or WBC), it consists of:

(1) simultaneous labeling of said viable bacteria and said white blood cells (WBC) present in said urine specimen, with a fluorescent viability marker of bacteria, said marker tagging and accumulating in both bacteria and white blood cells, under the same conditions (i.e concentration of marker, pH and temperature) and leading to different fluorescent elements;

(2) automatically counting all the fluorescent elements by photoelectric detection of the fluorescent marker; and (3) simultaneously classifying said fluorescent elements in fluorescent viable bacteria and in fluorescent white blood cells, in view to obtain in one part the total number of bacteria and on the other part, the total number of white blood cells, on the basis of their size.

The instant process allows, unexpectedly, to combine the simultaneous detection of bacteria and white blood cells with the discrimination made on the basis of fluorescent signal amplitude.

Advantageously, said size is evaluated, for instance, by measuring the fluorescent intensity, the scattering light intensity or aperture impedance of the different fluorescent elements.

According to one advantageous mode of carrying out said method, said viability marker of bacteria of step (1) is selected in the group consisting of products made fluorescent by an intracelluar enzyme, for instance a nonspecific esterase or a phosphatase.

According to another advantageous mode of carrying out said method, step (1) comprises, when said viability marker of bacteria is made fluorescent by an intracellular nonspecific esterase, incubating a urine specimen with a solution of carboxyfluorescein diacetate at 0.1–0.5%, at neutral pH.

Preferably in such a case, said incubation step includes a first incubation of 5–15 minutes, preferably 10 minutes at 37° C. followed by a second incubation of 5–15 minutes, preferably 10 minutes at 4° C.

According to another advantageous mode of carrying out said method, when said labeling is performed on a nonsedimented sample of urine, steps (2) and (3) (said counting and said classification) are carried out by flow cytometry.

In alternative, said method consists of:

(1) quantitative concentration of the urine specimen by filtering a known quantity of said sample through a filter with pore size small enough to retain both bacteria and white blood cells, (2) labeling the elements retained on said filter as described hereabove, (3) counting and classifying fluorescent elements on the whole filter by means of an appropriate scanning cytometer, such as to obtain on one part the number of fluorescent bacteria and on the other part, the number of fluorescent leucocytes, on the basis of their size and (4) calculating the concentration of bacteria and of leucocytes, present in the initial urine specimen by dividing the obtained numbers by the volume of urine filtered, to express them in terms of concentration in the original specimen.

According to the instant invention, said scanning cytometer is such as the one described in the European Patent 0 333 561.

In the instant invention, the detection of both bacteria and leucocytes are made rapidly and simultaneously on the same specimens.

Rapid determination of viable bacteria is enabled by elimination of the growth phase in favor of a direct approach for determination and quantitation of the viability of the microorganisms.

For instance, in the instant method, as specified hereabove, when the viability marker is made fluorescent by an intracellular nonspecific esterase, said intracellular enzyme of the viable microorganisms is able to catalyze a reaction resulting in the transformation of a fluorescein containing molecule from a non-fluorescent to a fluorescent state.

The fluorescent product is created and accumulated in the cell within minutes resulting in a fluorescent tag for viable bacteria.

The simultaneous measurement of bacteria and leucocytes is enabled by the use of an enzyme for the viability test which is also a common leucocyte enzyme (nonspecific esterase or phosphatase).

In this way, the majority of white blood cells will also be rendered fluorescent when their intracellular enzyme performs the same transformation on the fluorescein containing molecule.

Thus, unexpectedly, a single chemical preparation allows the simultaneous labeling of both leucocytes and viable bacteria in the sample of urine to be analyzed.

These fluorescent elements can then be counted and classified on the basis of their size, since the volume of leucocytes (100 femtoliters to 200 femtoliters) is much greater than the volume of bacteria which is typically less than 1 femtoliter.

The instant process allows, unexpectedly, to combine the simultaneous detection of bacteria and white blood cells with the discrimination made on the basis of fluorescent signal amplitude.

In the invention, enhancement of the sensitivity of the method to both white blood cells and bacteria is furthermore significatively increased by incorporation of a step of quantitative filtration, prior to said labeling.

In this process, a known volume of urine, as specified hereabove, is filtered through a membrane capable of retaining both bacteria and blood cells. The membrane is then treated chemically, as described above, to render the viable bacteria and white blood cells fluorescent. The entire membrane is then scanned rapidly and the different fluorescent elements are counted and classified.

The resulting cell counts are then be restored to a quantitative concentration determination by dividing the number obtained in scanning the entire membrane by the volume of urine filtered.

Unexpectedly the invention allows to simultaneously label viable bacteria and leucocytes in a single urine sample and also allows by use of a filtering membrane to obtain a quantitative measure.

Apart from the foregoing provisions, the invention also includes other provisions which will become apparent from the following description referring to examples of carrying out the method forming the subject of the present invention.

It must be clearly understood, however, that these examples are given solely in order to illustrate the subject of the invention without in any way implying a limitation.

EXAMPLE 1

Bacteria and leucocyte detection in urine using a flow cytometer.

3 ml of urine sample from healthy donor were spiked with bacteria ($10^7$/ml stock solution *E. coli*) and human blood leucocyte and diluted with 3 ml of labeling buffer (Hepes 10 mM, NaCl 140 mM, pH 7,3); 60 $\mu$l of a stock solution of carboxyfluorescein diacetate (10 mg/ml) are added to the diluted urine. Sample is incubated 10 minutes at 37° C. in a water bath, following by 10 minutes at 4° C. in an ice bath.

15 ml of labeling buffer are added and the labeled suspension is centrifuged 5 minutes at 1 800 rpm. The supernatant is discarded and the pellet is resuspended in 3 ml of cold labeling buffer and immediately after sample is injected in a flow cytometer at a flow rate of 10 $\mu$l/min where it is exposed to an argon laser light. Acquisition is performed on $10^4$ events, and the resulting fluorescence of the cells are quantified and classified according to their intensity as shown in FIGS. 1 and 2, in which the x axis represent the fluorescent intensity channel and the ordinate the number of fluorescent cells in each channel.

As shown in said figures with two samples spiked at two different bacteria/leucocyte ratio, bacteria and leucocytes are displayed in two different channel windows, where they can be counted using appropriate software.

Figure 2:
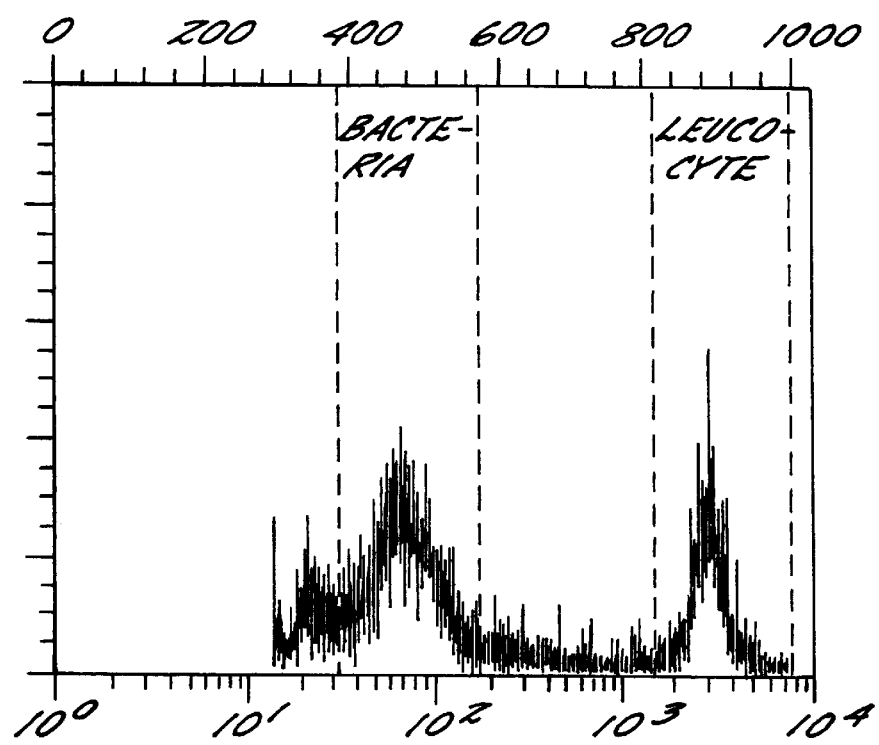
FIG. 2 is a graph showing fluorescence of a another urine sample spiked with a bacteria and human blood leukocytes.

In the FIG. 1, 51% of count are classified as bacteria, 26% as leucocyte. In the FIG. 2, 33% of count are classified as bacteria, 40% as leucocyte.

EXAMPLE 2

Bacteria and leucocyte detection in urine using a laser scan cytometer.

Urine samples are spiked as in example 1 but at a much lower concentration ($10^2$/ml) due to the better sensitivity of the laser scan (down to 1 cell per filter). 1 ml of spiked urine is filtered through a 0.22 $\mu$m per size filter membrane. 1 ml of labeling solution is added to the membrane and incubated 15 min at 25° C. Then the labeling solution is removed by filtration followed by a washing step with 4 ml of the labeling buffer. The membrane filter is introduced in the laser scan and analysed as described in EP Patent no 0 333 561. The result is shown in FIGS. 3a–c.

FIG. 3 represents the analysis of a sample spiked: (a) with bacteria, (b) with human leucocytes, and (c) with both bacteria and leucocytes. As shown, bacteria and human cells can be easily differentiated, according to their size, by the analysis of their respective fluorescence pulse length.

As is apparent from the foregoing description, the invention is in no way limited to those modes of execution, embodiments and modes of application which have now been described more explicitly; on the contrary, it encompasses all the variants thereof which may occur to those skilled in the Art, without deviating from the framework of the scope of the present invention.

We claim:

1. A method for the rapid and simultaneous counting of both viable bacteria and white blood cells in a fluid sample, comprising the steps of:
    (a) simultaneous labeling of said bacteria and said white blood cells present in said fluid sample, with a fluorescent viability marker of bacteria, said viability marker being selected from a member of the group consisting of a non-specific esterase and a phosphatase, said marker tagging and accumulating in both bacteria and white blood cells, under the same conditions and leading to different fluorescent elements;
    (b) automatically counting all the fluorescent elements by photoelectric detection of the fluorescent marker; and
    (c) simultaneously classifying said fluorescent elements in fluorescent viable bacteria and in fluorescent white blood cells to obtain the total number of white blood cells, on the basis of their size.

2. The method according to claim 1, wherein said viability marker of bacteria is made fluorescent by an intracellular non-specific esterase, and step (a) further comprises incubating said fluid sample with a solution of carboxyfluorescein diacetate at 0.1 to 0.5% at neutral pH.

3. The method according to claim 2 wherein said incubation step includes a first incubation of about 5 to about 15 minutes at 37° C., followed by a second incubation of 5 to 15 minutes at 4° C.

4. The method according to claim 1, wherein when said labeling is performed on a nonsedimented sample of said fluid and steps (b) and (c) are carried out by flow cytometry.

5. A method of analyzing a urine specimen wherein the rapid and simultaneous counting of both viable bacteria and white blood cells comprises:
   (a) quantitative concentration of said specimen by filtering a known quantity of said specimen through a filter with pore size small enough to retain bacteria and white blood cells;
   (b) simultaneous labeling of the elements retained on said filter, with a fluorescent viability marker of bacteria, said marker tagging and accumulating in both bacteria and white blood cells, under the same conditions and leading to different fluorescent elements;
   (c) counting and classifying fluorescent elements on the whole filter by means of an appropriate scanning cytometer, such as to obtain on one part the number of fluorescent bacteria and on the other part, the number of fluorescent leukocytes, on the basis of their size; and
   (d) calculating the concentration in bacteria and in leukocytes present in the initial urine sample by dividing the obtained counts by the volume of urine filtered, to express them in terms of concentration in the original sample.

6. The method according to claim 1, wherein the size of said fluorescent elements is evaluated either by measuring the fluorescent intensity or the scattering light intensity or aperture impedance of the different fluorescent elements.

7. The method according to claim 1 wherein said viability marker of bacteria is a non-specific esterase.

8. The method according to claim 1 wherein said viability marker of bacteria is a phosphatase.

9. The method according to claim 1 wherein prior to labeling a quantitative concentration of said fluid sample is provided by filtering a known quantity of said sample through a filter with pore size small enough to retain bacteria and white blood cells.

10. The method according to claim 1, wherein when said labeling is performed on a nonsedimented sample steps (b) and (c) are carried out by solid phase cytometry.

11. The method according to claim 5 wherein said viability marker of bacteria is a non-specific esterase.

12. The method according to claim 5 wherein said viability marker of bacteria is a phosphatase.

13. A method for the rapid and simultaneous counting of both viable bacteria and leukocytes in a urine specimen, comprising the steps of:
    (a) simultaneous labeling of said bacteria and said white blood cells present in said urine specimen, with a fluorescent viability marker of bacteria selected from the group consisting of products made fluorescent by an intracellular enzyme, said marker tagging and accumulating in both bacteria and white blood cells, under the same conditions and leading to different fluorescent elements;
    (b) automatically counting all the fluorescent elements by photoelectric detection of the fluorescent marker; and
    (c) simultaneously classifying said fluorescent elements in fluorescent viable bacteria and in fluorescent white blood cells to obtain the total number of bacteria and the total number of white blood cells, on the basis of their size.

14. The method according to claim 13 wherein prior to labeling a quantitative concentration of said body fluid is provided by filtering a known quantity of said sample through a filter with pore size small enough to retain bacteria and white blood cells.

15. The method according to claim 13 wherein said intracellular enzyme is a non-specific esterase.

16. The method according to claim 13 wherein said intracellular enzyme is a phosphatase.

17. The method according to claim 13, wherein step (a) comprises, when said viability marker of bacteria is made fluorescent by an intracellular non-specific esterase, incubating a urine specimen with a solution of carboxyfluorescein diacetate at 0.1–0.5% at neutral Ph.

18. The method according to claim 13 wherein said incubation step includes a first incubation of from 5 to 15 minutes at 37° C., followed by a second incubation of from 5 to 15 minutes at 4° C.

19. The method according to claim 13, wherein when said labeling is performed on a nonsedimented sample of urine and steps (b) and (c) are carried out by flow cytometry.

20. The method according to claim 13, wherein when said labeling is performed on a nonsedimented sample of urine and steps (b) and (c) are carried out by solid phase cytometry.

21. The method according to claim 13, wherein said viability marker of bacteria is made fluorescent by an intracellular non-specific esterase, and step (a) further comprises incubating said urine specimen with a solution of carboxyfluorescein diacetate at 0.1 to 0.5% at neutral pH.

22. The method according to claim 21 wherein said incubation step includes a first incubation of about 5 to about 15 minutes at 37° C., followed by a second incubation of 5 to 15 minutes at 4° C.

* * * * *